US006527723B2

(12) United States Patent
Ossmann et al.

(10) Patent No.: US 6,527,723 B2
(45) Date of Patent: Mar. 4, 2003

(54) VARIABLE MULTI-DIMENSIONAL APODIZATION CONTROL FOR ULTRASONIC TRANSDUCERS

(75) Inventors: William J. Ossmann, Acton, MA (US); McKee D. Poland, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/892,008

(22) Filed: Jun. 26, 2001

(65) Prior Publication Data

US 2002/0198455 A1 Dec. 26, 2002

(51) Int. Cl.[7] .................................................. A61B 8/00

(52) U.S. Cl. ........................ 600/459; 600/447; 600/437; 73/602; 128/916; 367/138; 367/157

(58) Field of Search ................................. 600/437, 443, 600/444, 447, 449, 458, 459, 463; 73/602, 606, 607; 367/138, 153, 155, 157; 128/916

(56) References Cited

U.S. PATENT DOCUMENTS 5,349,359 A * 9/1994 Dallaire et al. ............. 342/195
5,647,365 A * 7/1997 Abboud ........................ 73/626
5,686,922 A * 11/1997 Stankwitz et al. .......... 342/196
6,066,099 A * 5/2000 Thomenius et al. ........ 600/447
6,138,513 A * 10/2000 Barabash et al. ............. 73/602
6,193,659 B1 * 2/2001 Ramamurthy et al. ...... 600/443
6,381,197 B1 * 4/2002 Savord et al. .............. 367/178

* cited by examiner

*Primary Examiner*—Philip H. Leung
(74) *Attorney, Agent, or Firm*—John Vodopia

(57) ABSTRACT

Variable multi-dimensional apodization control for an ultrasonic transducer array is disclosed. The variable multi-dimensional apodization control is applicable to both piezoelectric based transducers and to MUT based transducers and allows control of the apodization profile of an ultrasonic transducer array having elements arranged in more than one dimension.

22 Claims, 6 Drawing Sheets

VARIABLE MULTI-DIMENSIONAL APODIZATION CONTROL FOR ULTRASONIC TRANSDUCERS

TECHNICAL FIELD

The invention relates generally to ultrasonic transducers, and, more particularly, to a system for variable multi-dimensional apodization control in an ultrasonic transducer.

BACKGROUND OF THE INVENTION

Ultrasonic transducers have been available for quite some time and are useful for interrogating solids, liquids and gasses. One particular use for ultrasonic transducers has been in the area of medical imaging. Ultrasonic transducers can be formed of piezoelectric elements or can be fabricated on a semiconductor substrate, in which case the transducer is referred to as a micromachined ultrasonic transducer (MUT). Piezoelectric transducer elements typically are made of material such as lead zirconate titanate (abbreviated as PZT), with a plurality of elements arranged to form a transducer assembly. MUTs are fabricated using various semiconductor substrate materials resulting in a capacitive non-linear ultrasonic transducer that comprises, in essence, a flexible membrane supported around its edges over a semiconductor substrate. By applying contact material to the membrane (or a portion of the membrane) and to the semiconductor substrate, and then by applying appropriate voltage signals to the contacts, the MUT may be energized such that an appropriate ultrasonic wave is produced. Similarly, with the application of a bias voltage, the membrane of the MUT may be used to generate receive ultrasonic signals by capturing reflected ultrasonic energy and transforming that energy into movement of the membrane, which then generates a receive signal. Whether constructed using piezoelectric elements or MUT elements, the transducer assembly is then further assembled into a housing, possibly including control electronics in the form of electronic circuit boards, the combination of which forms an ultrasonic probe. This ultrasonic probe, which may include acoustic matching layers between the surface of the piezoelectric transducer element or elements and the probe body, may then be used to send and receive ultrasonic signals through body tissue.

Regardless of whether the transducer is constructed using piezoelectric elements or MUT elements, in operation it is possible to shape the transmit and receive signals based upon the type of imaging being performed. This is possible because in modern transducers each element in the transducer array is typically connected to the control electronics. In some imaging applications, it is desirable to operate only a portion of the total number of elements in the array at any time. This is referred to as controlling the aperture of the transducer array. The aperture of the transducer array refers to the configuration of the transducer elements that are active at any moment. The electronic control of each element in the transducer allows the transmit and receive signals to be shaped to provide an appropriate signal for the type of imaging being performed. For example, by controlling the transmit energy supplied to some or all of the elements (commonly referred to as "transmit beamforming") the ultrasonic interrogation pulse sent into the subject can be shaped to provide, for example, high resolution at various depths. Similarly, by electronically altering the receive energy (referred to as "receive beamforming") the received energy can be used to form high quality images at various depths and through various types of tissue.

Various imaging parameters of the ultrasonic transducer can be controlled by varying the transmit energy and operating on the receive energy. For example, by performing transmit and receive beamforming, the elevation and depth of the ultrasonic beam can be varied to provide various lateral and elevation steering angles and various interrogation depths. One manner of controlling the transducer elements is known as "apodization." Apodization of an ultrasonic transducer aperture is a gradual reduction of the transmit amplitude and/or receive gain from the center of the aperture to the edges of the aperture with a resultant decrease in beam side lobe levels. In a transmit beam, there is a main energy beam in the direction of interrogation and sidelobe energy located at predictable angles from the main beam direction. These side lobes cause smearing of objects in the image, increase clutter, and reduce contrast. Therefore, it is generally desirable to maximize the transmit energy in the desired direction and reduce the sidelobe energy to levels at which the sidelobe energy will not interfere with the main energy beam. Apodization trades sensitivity and beam width for beam sidelobe levels.

Current ultrasonic transducers have been limited in the amount of apodization control available. Typically, current systems allow apodization control only on one dimension of the transducer. Apodization control in the other dimension (assuming a two-dimensional transducer) is either not performed or is a non-varying function of the first dimension of the transducer. Other systems approximate two-dimensional apodization control by using what is referred to as a "sparse array" in which less than all of the elements in the array are connected to the transmit and receive electronics. Apodization in a sparse array is achieved by decreasing the density of the active transducer elements from the center of the array toward the edges of the array. Unfortunately, the sparse array is constrained so that many elements on the transducer array are unavailable for forming an apodization pattern because they are not connected to the transmitters and receivers. Furthermore, since many of the elements in a sparse array are not connected, the maximum sensitivity of a sparse array will be less than that of a fully sampled array.

In transducer arrangements having fixed or limited apodization control, the tradeoffs between sensitivity, beam width, and beam sidelobe levels cannot be optimized for particular imaging applications. Furthermore, a fixed apodization is optimal only for a particular aperture size of a given transducer. If a different aperture is used, the apodization pattern will be the wrong size. Fixed apodization also fails to allow different apodization profiles to be used for transmit and receive apertures. Fixed elevation apodization restricts the overall aperture apodization to functions that can be separated (i.e. factored) into a product of two functions, one being a function of only the elevation dimension and the other being a function of only the lateral dimension. This is known mathematically as a separable function of the two dimensions of the aperture. Separable apodization functions tend to have beam patterns that concentrate the side lobe energy along the two dimensions by which the function can be separated. It would be advantageous if the side lobe energy could be redistributed in a circularly symmetric manner about the main beam. This would lower the overall side lobe level and even out the influence of the side lobe energy with respect to all areas adjacent to the main beam. Creating a circularly symmetric beam pattern requires a circularly symmetric aperture apodization, which except for a few special cases is not possible using separable functions. Therefore, it would be desirable to have an ultrasonic transducer array in which the apodization function may be a non-separable function of the two dimensions.

When sparse arrays are operated to provide a fixed apodization of the aperture based only on the density of the active elements, they share most of the same drawbacks as transducers having fixed elevation apodization, thus extending the drawbacks to both dimensions of the transducer. Additionally, the amplitude control in a sparse array tends to be crude, relying only on the density of active elements. The transmit and receive amplitudes of the active elements in a sparse array can be controlled, but only those elements actually connected to the transmit/receive electronics can be used, thus constraining the precision with which the apodization pattern can be specified. Furthermore, due to undersampling of the aperture, while sparse arrays tend to improve the side lobe performance of the array at close-in steering angles, the side lobe performance degrades significantly at larger steering angles.

Therefore, it would be desirable to have an ultrasonic transducer array in which variable multi-dimensional apodization control is possible.

SUMMARY

Variable multi-dimensional apodization control for an ultrasonic transducer array allows all dimensions of an ultrasonic transducer array to have variable apodization control. The variable multi-dimensional apodization control is applicable to both piezoelectric based transducers and to MUT based transducers and allows control of the apodization profile of an ultrasonic transducer array having elements arranged in more than one dimension.

Other systems, methods, features, and advantages of the invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention, as defined in the claims, can be better understood with reference to the following drawings. The components within the drawings are not necessarily to scale relative to each other, emphasis instead being placed upon clearly illustrating the principles of the present invention.

DETAILED DESCRIPTION OF THE INVENTION

The invention to be described hereafter is applicable to all types of ultrasonic transducer elements. Furthermore, for simplicity in the following description, only the principal elements of an ultrasonic transducer and related control circuitry are illustrated.

Prior to discussing the invention, a brief discussion of ultrasonic transducer aperture and apodization control will be useful. Therefore, FIGS. 1A and 1B collectively illustrate the effect of transmit apodization aperture control.

Figure 1A:
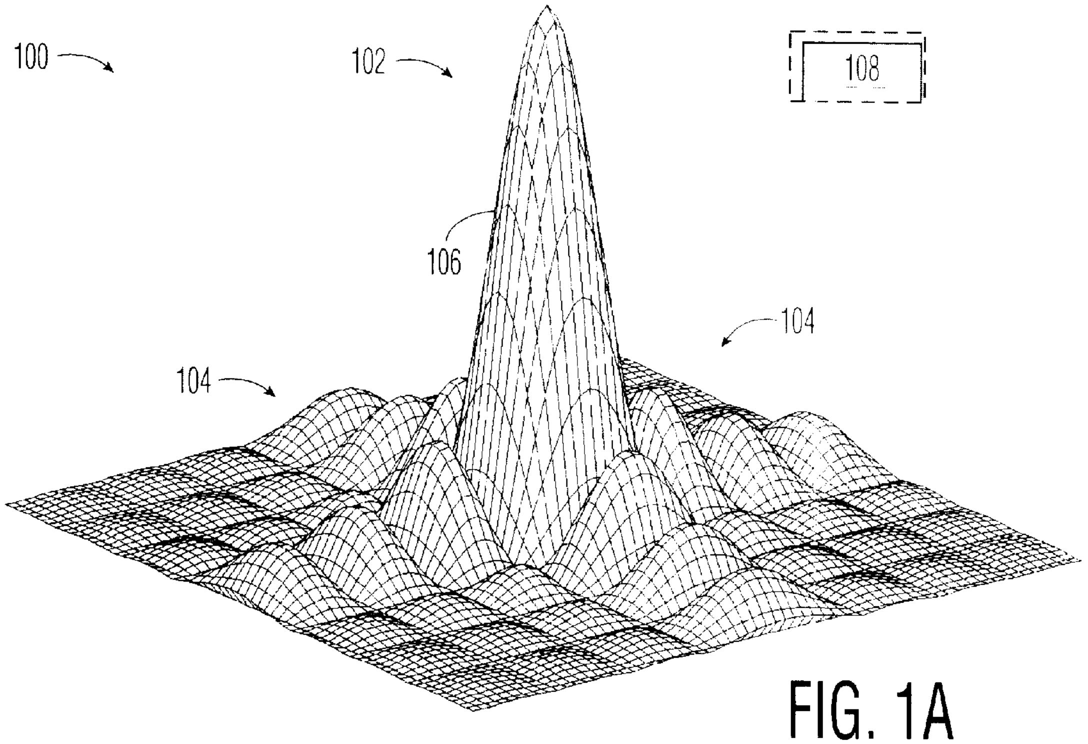
FIG. 1A is a graphical illustration showing the beam plot of an ultrasonic transducer array in which all transducer elements in the aperture are uniformly excited with the same input signal.

FIG. 1A is a graphical illustration 100 showing the beam plot of an ultrasonic transducer array in which all transducer elements in the aperture are uniformly excited with the same input signal. The beamplot illustrates a transmit signal emanating from an ultrasonic transducer. The beamplot includes a main lobe 102 located at an approximate 0° beam steering angle. Although the majority of the ultrasonic energy is directed within a few degrees plus or minus of the 0° beam steering angle resulting in the main lobe 102, energy is also directed at angles between −90° and +90°. This off 0° energy shows up in the beam plot as side lobes 104. As illustrated in FIG. 1A, the side lobes 104 that are closer to the main lobe 102 are higher in amplitude than the side lobes 104 that are further away from the main lobe 102. The beam plot 100 results when each element in an ultrasonic transducer array aperture is uniformly excited with the same amplitude, as illustrated by the transducer element apodization plot 108. The plot 108 illustrates the situation in which each element in the transducer array is excited with the stimulus signal at the same amplitude. One manner of reducing the side lobe energy close to the main lobe 102 is by adjusting the apodization of the aperture. An example of an aperture having such apodization is illustrated in FIG. 1B.

Figure 1B:
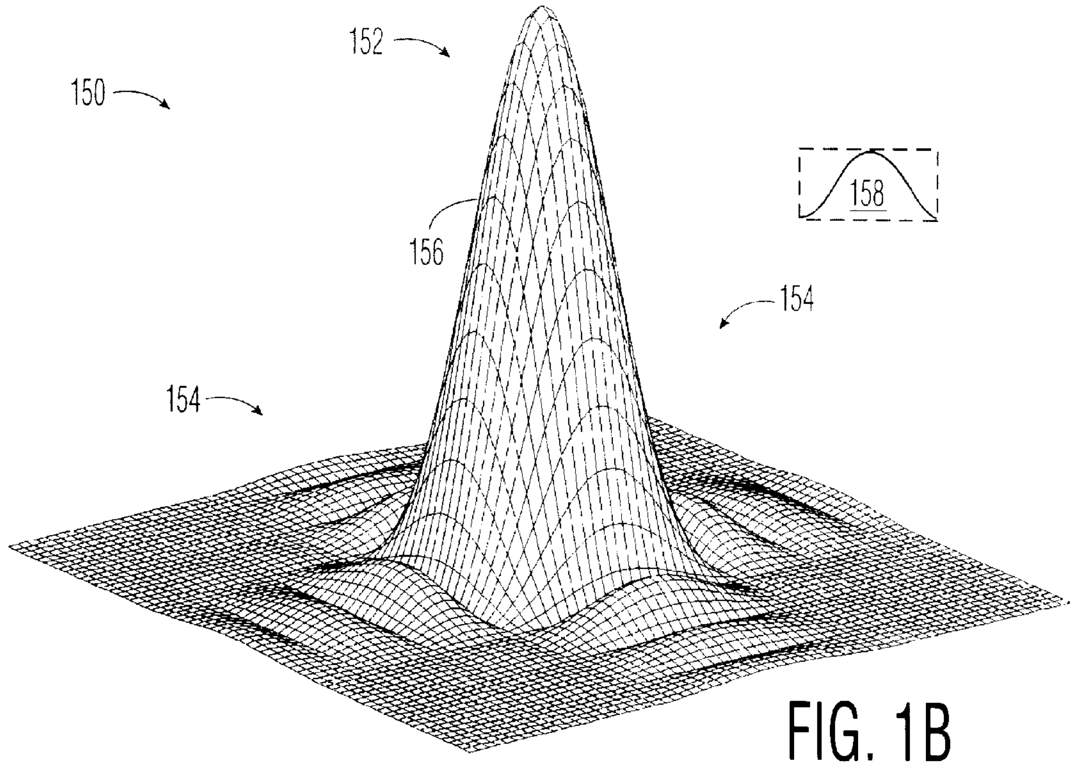
FIG. 1B is a graphical illustration showing a beam plot of an ultrasonic transducer array in which apodization control has been applied to the aperture.

FIG. 1B is a graphical illustration 150 showing a beam plot of an ultrasonic transducer array in which apodization control has been applied to the aperture. In FIG. 1B, the main lobe 152 has lower amplitude than the main lobe 102 of FIG. 1A and also exhibits a beam width 156 that is wider than the beam width 106 of the main lobe 102 of FIG. 1A. The main lobe 152 has a wider beam width and lower amplitude than the main lobe 102 of FIG. 1A resulting in lower transducer sensitivity. However, one of the benefits of the configuration shown in FIG. 1B is that the level of the side lobes 154 is significantly lower than the level of the side lobes 104 of FIG. 1A. This situation occurs because apodization has been applied to the transducer elements in the aperture.

With the apodization profile illustrated in FIG. 1B, the elements toward the center of the aperture transmit at full strength, but the elements toward the edges of the aperture transmit at reduced strength, thereby shaping the ultrasonic transducer aperture so that the side lobe energy is significantly reduced. Such an apodization profile is illustrated by the apodization plot 158. Although illustrated using a transmit function, this apodization control of the aperture is also effective on receive cycles. To control apodization on receive cycles, the respective gain applied to each element within an ultrasonic transducer array is varied according to a desired apodization profile.

Figure 2:
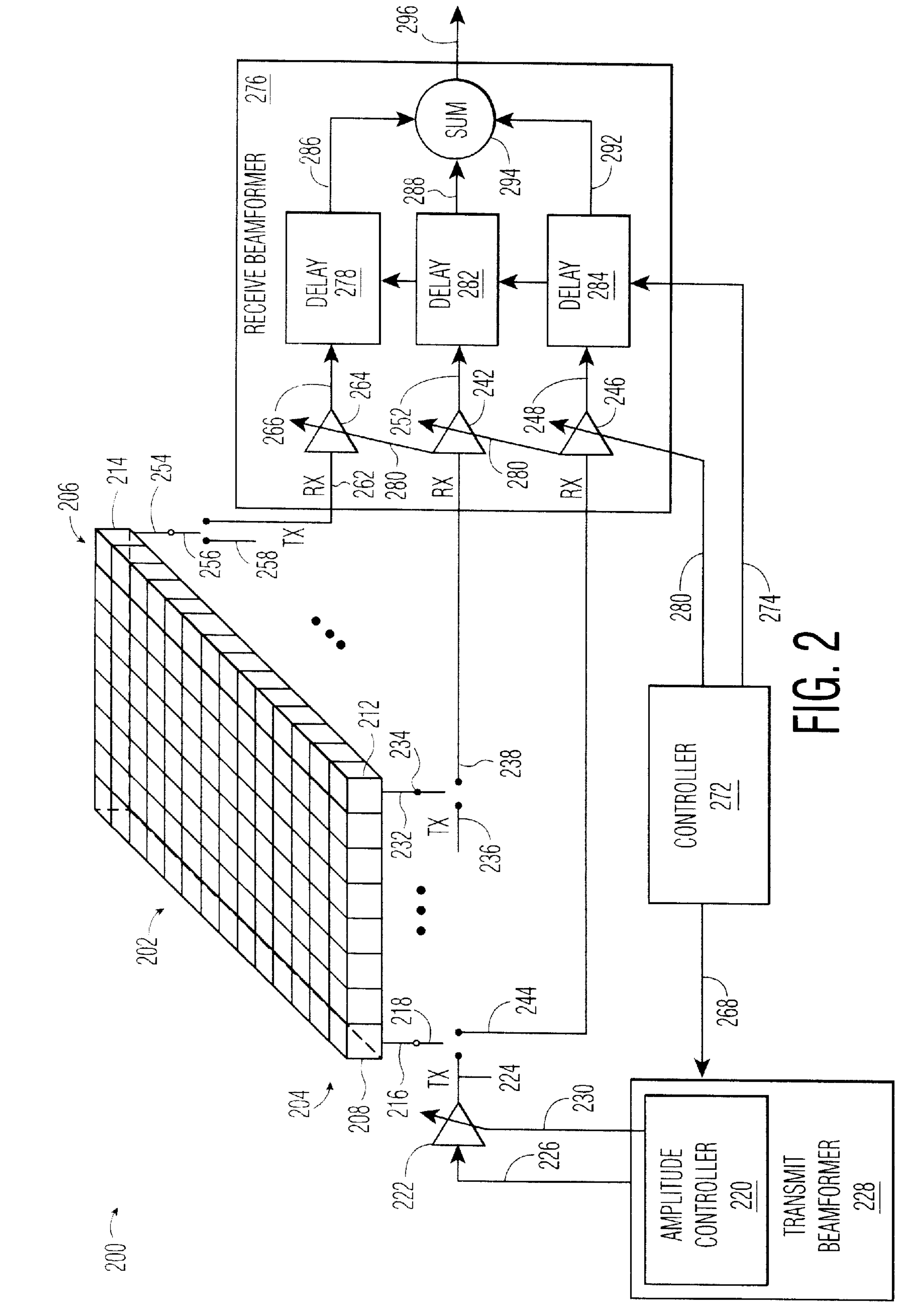
FIG. 2 is a schematic view illustrating an apodization control system constructed in accordance with an aspect of an embodiment of the invention.

FIG. 2 is a schematic view illustrating an apodization control system 200 constructed in accordance with an aspect of an embodiment of the invention. The apodization control system 200 employs a multi-dimensional transducer array 202. In the embodiment shown in FIG. 2, the transducer array 202 is depicted as a two-dimensional transducer array that includes a plurality of ultrasonic transducer elements, exemplar ones of which are illustrated using reference numerals 208, 212 and 214.

The ultrasonic transducer elements 208, 212 and 214 are arranged in rows and columns, exemplar ones of which are illustrated using reference numerals 204 and 206, respectively. Such a configuration is sometimes referred to as a matrix array. However, other transducer element configurations are possible. Although illustrated using a planar 8×14 array of ultrasonic transducer elements, the concepts of the invention are applicable to any two-dimensional ultrasonic transducer array configuration, including configurations in which one or both of the two dimensions is curved. For example, two-dimensional transducer arrays having cylindrical, spherical, toroidal, or other curved surfaces are possible and may benefit from the concepts of certain aspects of the preferred embodiment of the invention. Because the curvature of the array bends the array into the third dimension, such transducer arrays may also be considered to be three-dimensional, and the apodization control thereof may also be considered to be three-dimensional.

In accordance with an aspect of a preferred embodiment of the invention, each of the elements 208, 212 and 214 of the multi-dimensional transducer array 200 is individually controllable. Specifically, each of the transducer elements 208, 212 and 214 can function as a transmit element and as a receive element, and receives individual control signals. For example, ultrasonic transducer element 208 connects via connection 216 to a transmit/receive (T/R) switch 218. The T/R switch 218 is controlled by a signal (not shown) from the controller 272 to allow the transducer element 208 to function in a transmit mode and in a receive mode.

When the ultrasonic transducer element 208 is used in a transmit mode, the ultrasonic transducer element 208 receives a transmit pulse from the transmit beamformer 228 through connection 226 and via the variable amplifier 222 via connection 224. The variable amplifier 222 is used to define the characteristics of the transmit pulse applied to the ultrasonic transducer element 208 and is controlled by amplitude controller 220 via connection 230. Although omitted for simplicity, each element in the two-dimensional transducer array 202 includes a similarly controlled variable amplifier. When the ultrasonic transducer element 208 is used in a receive mode, ultrasonic energy that impinges upon the surface of the ultrasonic transducer element 208 is converted to an electrical signal. The electrical signal is communicated via connection 216, through T/R switch 218 (which is now connected to connection 244 by operation of a control signal from controller 272) so that the receive signal is applied to variable gain amplifier 246. The variable gain amplifier 246 amplifies the electrical receive signal and supplies the signal over connection 248 to delay element 284.

In a similar manner, the ultrasonic transducer element 212 receives a transmit pulse via connection 236 and supplies a receive signal via connection 238 to variable gain amplifier 242. Variable gain amplifier 242 supplies the receive signal via connection 258 to delay element 282. Similarly, ultrasonic transducer element 214 receives a transmit signal via connection 258, through switch 256 and connection 254, while the receive signal is passed via connection 254, through switch 256 and connection 262 to variable gain amplifier 264. The variable gain amplifier 264 supplies the amplified receive signal on connection 266 to the delay element 278. Each element in the multi-dimensional transducer array 202 is thus controlled, thereby allowing full apodization control over each element in the multi-dimensional transducer array 202.

The variable gain amplifiers 262, 242 and 246, and the delay elements 278, 282 and 284 are all contained within receive beamformer 276. While shown as having only three variable gain amplifiers and three delay elements, the receive beamformer 276 includes sufficient amplifiers and delay element circuitry (and other processing circuitry) for each of the ultrasonic transducer elements in the multi-dimensional transducer array 202. Furthermore, various multiplexing, sub-beamforming, and other signal processing techniques can be performed by the receive beamformer 276. However, for ease of explanation, the receive beamformer in FIG. 2 includes only three delay elements.

Each of the amplifiers in the receive beamformer is controlled by a signal via connection 280 from the controller 272. The signal on connection 280 determines the receive gain applied by each of the variable gain amplifiers 264, 242 and 246. The gain applied by each of the amplifiers may vary. Similarly, each delay element 278, 282 and 284 is programmed by a signal from the controller 272 via connection 274. This control signal determines the amount of delay that each of the delay elements 278, 282, and 284 applies to its respective receive signal. In this manner, apodization of the receive aperture can be controlled with a high degree of precision, because each ultrasonic transducer element 208, 212 and 214 in the two-dimensional transducer array 202 is coupled to a respective variable gain amplifier 246, 242 and 264. Further, each variable gain amplifier receives, from controller 272, a signal that determines the amount of gain to apply to each receive signal.

The outputs of delay elements 278, 282 and 284 are respectively supplied via connections 286, 288 and 292 to summing element 294. Summing element 294 combines these outputs and supplies a beamformed signal on connection 296 to additional processing elements, such as microprocessor processing circuitry, display circuitry, and other control circuitry (not shown). In alternative configurations, the variable gain amplifiers 264, 242 and 246 may be located after the delay elements 278, 282 and 284, respectively. Further, the outputs of the delay elements 278, 282 and 284 may be combined into sub-arrays and variable gains may be applied to each sub-array either before or after the sub-array signal passes through its respective delay prior to the summing element 294.

The multi-dimensional transducer array 202 having individually controllable transducer elements 208, 212 and 214 makes the apodization pattern variable in multiple dimensions. Specifically, the apodization of the multi-dimensional transducer array 202 can be individually controlled with respect to the position of each element within the array. By having complete control over the entire aperture, the apodization control system 200 allows the beam plot of the aperture to be controlled with a high degree of precision.

Furthermore, the arrangement shown in FIG. 2 allows a fully sampled, controllable, arbitrary (specified without restraint) multi-dimensional apodization profile to be applied to the multi-dimensional transducer array 202. The term "fully sampled" relates to each ultrasonic transducer element 204, 212 and 214 being individually controllable. In such an arrangement, there are no instances in which individual elements of the multi-dimensional transducer array 202 will not receive some manner of control signal from the controller 272. The apodization of the multi-dimensional transducer array aperture is an arbitrary, fully sampled, controllable function of both dimensions of the aperture. The apodization may be adjusted to fit the size of the active aperture and the amount of apodization may be varied to suit varying imaging conditions.

Furthermore, the apodization may be varied between transmit and receive cycles, or may be varied during different receive cycles. Furthermore, the multi-dimensional transducer array 202 may be partially sampled, in which not every element is part of the active aperture. Further still, the apodization may be a function f(x,y) of the two-dimensions of the aperture that cannot be expressed as a product of two simpler functions, g(x)×h(y), one being a function only of one dimension and the other being a function only of the other dimension of the aperture. This is known mathematically as a non-separable function of the two dimensions. Non-separable apodization functions include, as a subset, most functions with circular symmetry. Circularly symmetric apodization functions are advantageous in that the beam side lobe energy is distributed in a circularly symmetric pattern, and is therefore more uniform and of a generally lower level than for a separable apodization function. This will be illustrated below with respect to FIGS. 5A and 5B.

Figure 3:
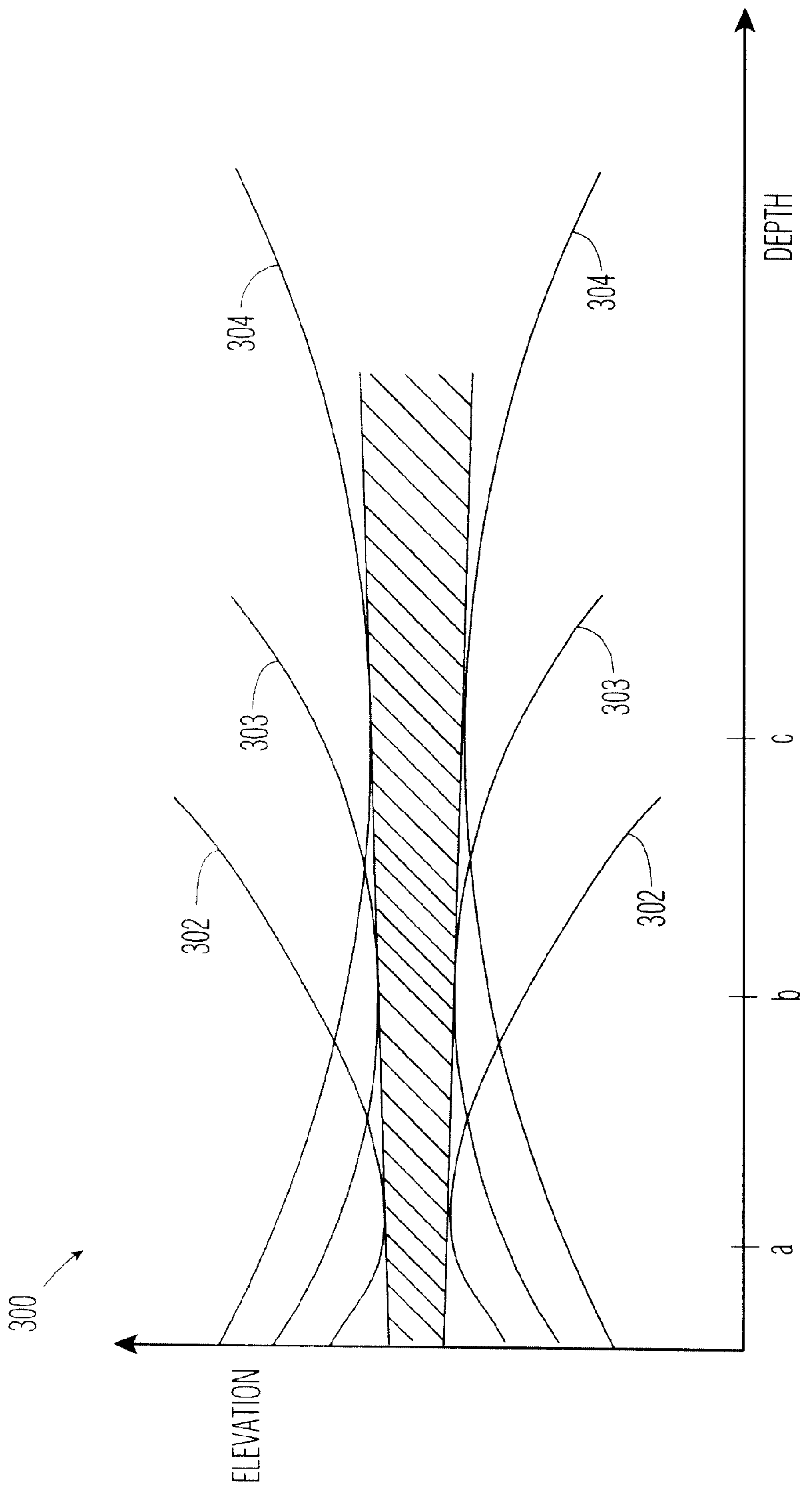
FIG. 3 is a graphical illustration showing the effect on an ultrasound beam of varying the apodization control with respect to depth on the aperture of the two-dimensional ultrasonic transducer array of FIG. 2.

FIG. 3 is a graphical illustration 300 showing the effect on an ultrasound beam of varying the apodization control with respect to depth on the aperture of the multi-dimensional ultrasonic transducer array 202 of FIG. 2. The vertical axis represents the elevation angle of the aperture and the horizontal axis represents depth of imaging. Curve 304 illustrates a condition in which a large aperture is used for imaging. As shown, a wide field converges at a certain depth, denoted by point c, into a narrow image field and then diverges. Such a configuration is useful for deep imaging.

Alternatively, curve 302 illustrates the situation in which a small aperture is used for imaging. As shown in curve 302, a much narrower beam occurs at a shallower depth of interest, denoted by point a, than that of curve 304. Such an aperture is useful for imaging at shallower depths. Furthermore, in accordance with an aspect of the preferred embodiment of the invention, it may be desirable to maximize the range of depths of interest available with a single transmit pulse. The range of depths of interest may be maximized by transmitting with an aperture size and apodization, the beam characteristics of which are intermediate between curve 302 and curve 304, for example, curve 303. Curve 303 focuses at point b. Then, the receive cycle can be started using a narrow beam (i.e., a small aperture) represented by curve 302 and then increasing to a larger aperture as illustrated using curve 304 in synchronicity with the arrival times of the returning echoes. This mode of operation is referred to as dynamic receive apodization. In this manner, the receive signals from every depth of interest are received by an aperture, the beamwidth of which is minimized for that depth, maximizing the range of depths over which good beam characteristics are achieved. The net effective receive beam at each depth is defined by the receive aperture apodization and beamforming delays used to receive the signals from that depth as exemplified by the curves 302, 303, and 304. In this manner, the range of depths of interest, as shown by the crosshatched lines, can be maximized.

Figure 4A:
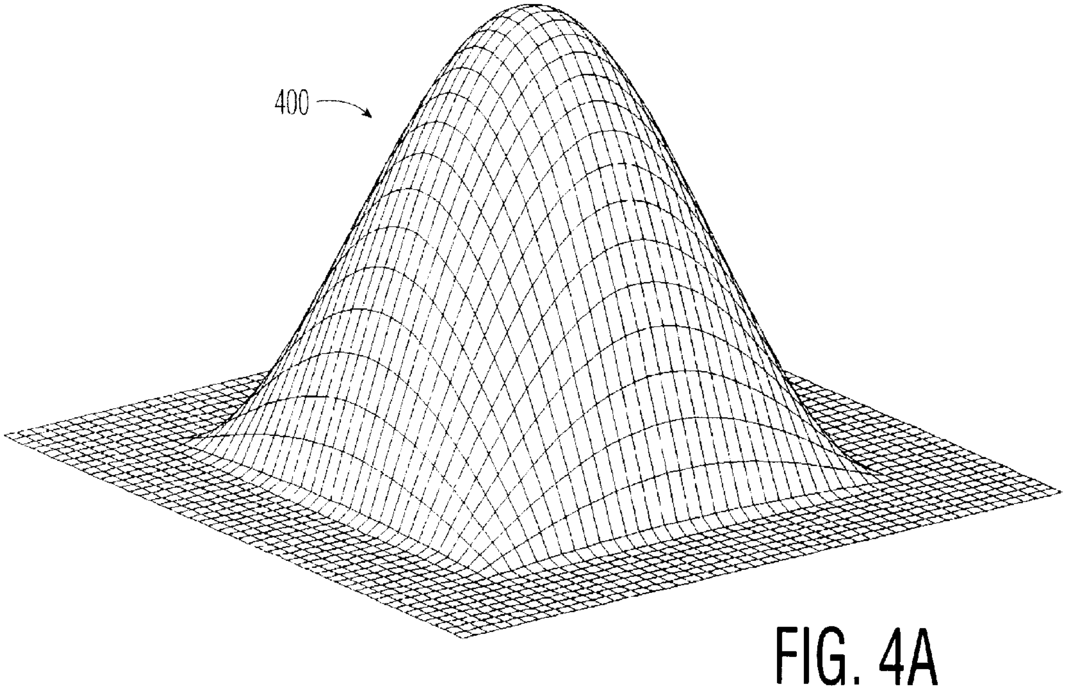
FIG. 4A is a graphical illustration showing the apodization profile of a transducer to which a separable apodization function has been applied.

FIG. 4A is a graphical illustration showing the apodization profile of a transducer to which a separable apodization function has been applied. As illustrated in FIG. 4A, the apodization profile 400 is a separable function and is expressed as a product of two simple functions, g(x)×h(y), one being a function only of one dimension and the other being a function only of the other dimension of the aperture. Unfortunately however, when limited to a separable apodization function, it is impossible to create a circular shaped apodization profile.

Figure 4B:
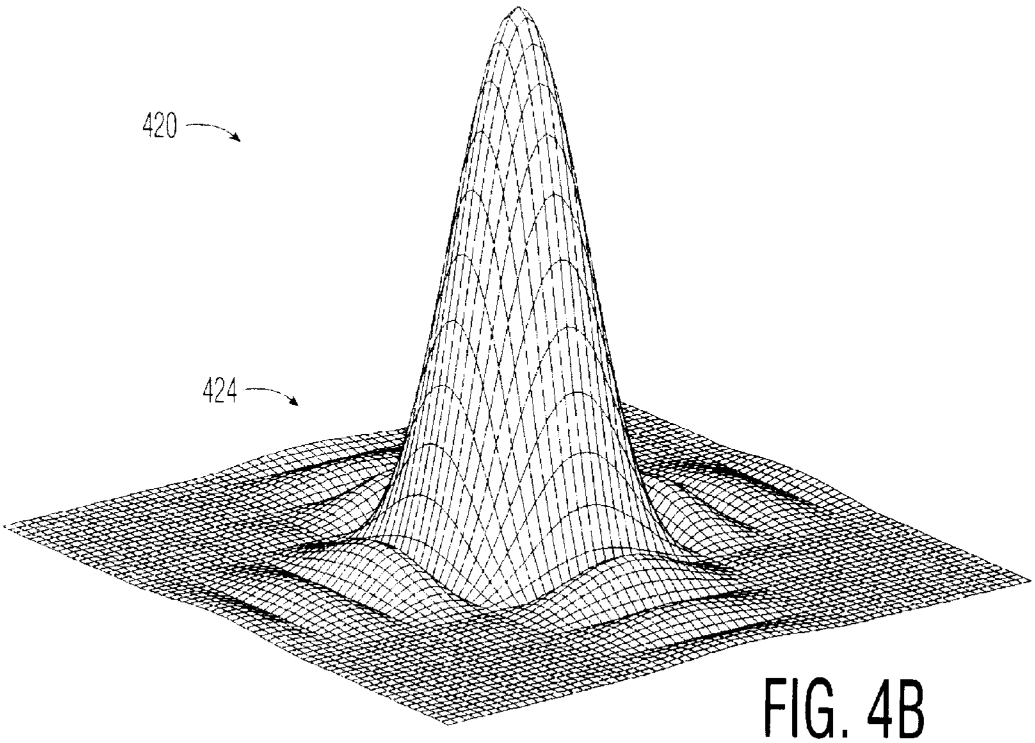
FIG. 4B is a graphical illustration showing a beam pattern for the separable apodization function of FIG. 4A.

FIG. 4B is a graphical illustration showing a beam pattern for the separable apodization function of FIG. 4A. As shown in FIG. 4B, the beam pattern 420 includes discontiguous side lobes 424 that result from the separable apodization function.

Figure 5A:
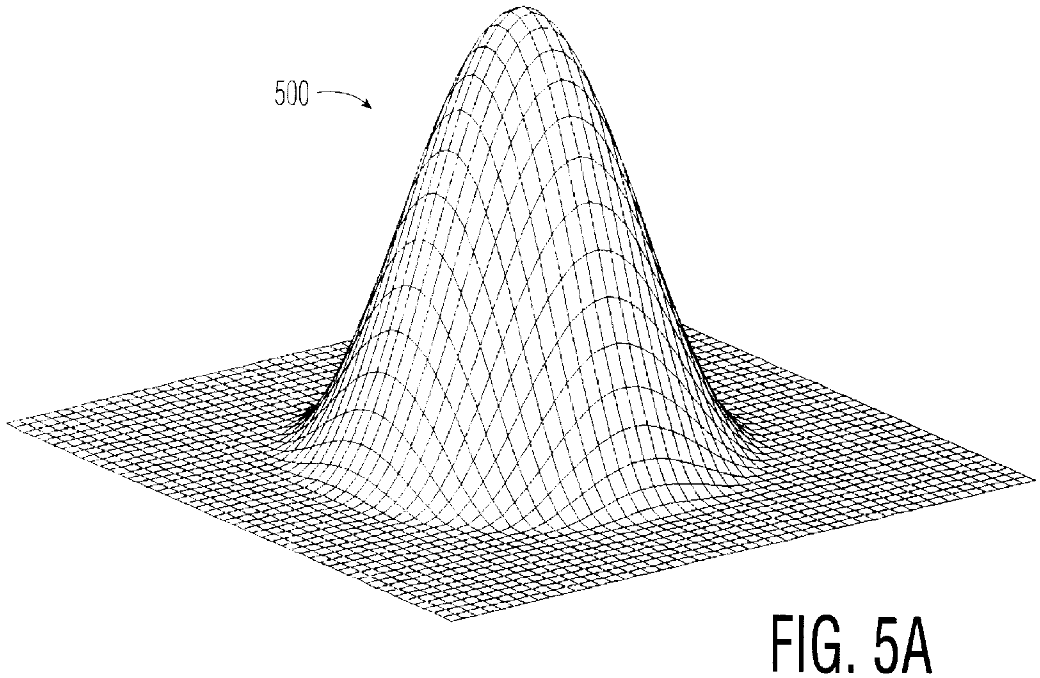
FIG. 5A is a graphical illustration showing an apodization profile of a transducer to which a non-separable apodization function has been applied.

FIG. 5A is a graphical illustration showing an apodization profile of a transducer to which a non-separable apodization function has been applied. As shown in FIG. 5A, the apodization profile 500 is a function of the complex function f(x, y) of the two dimensions of the aperture. As shown in FIG. 5A, it is possible to create a circular aperture when using a non-separable apodization function.

Figure 5B:
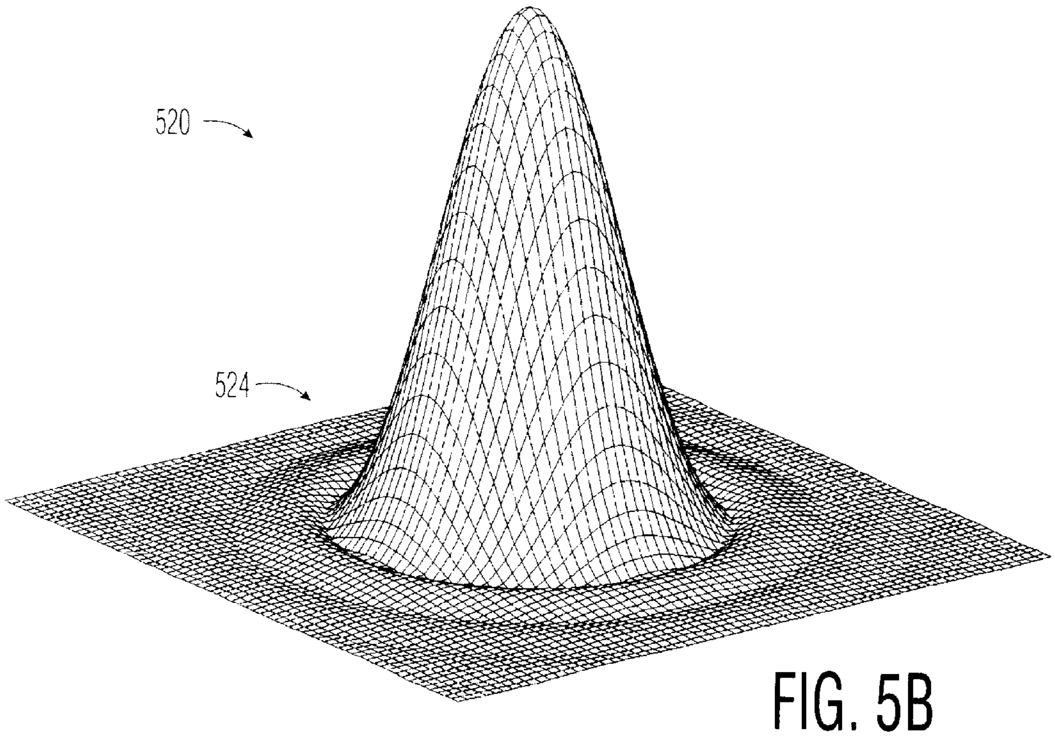
FIG. 5B is a graphical illustration showing the beam pattern that results from the non-separable apodization function of FIG. 5A.

FIG. 5B is a graphical illustration showing the beam pattern that results from the non-separable apodization function of FIG. 5A. The beam pattern 520 includes side lobes 524 that are circularly arranged with respect to the beam pattern 520. In this manner, the non-separable apodization function can be used to generate a beam pattern having a circular symmetry. Circularly symmetric apodization functions are advantageous in that the beam side lobe energy is distributed in a circularly symmetric pattern, and is therefore more uniform and of a generally lower level than for a separable apodization function.

Figure 6:
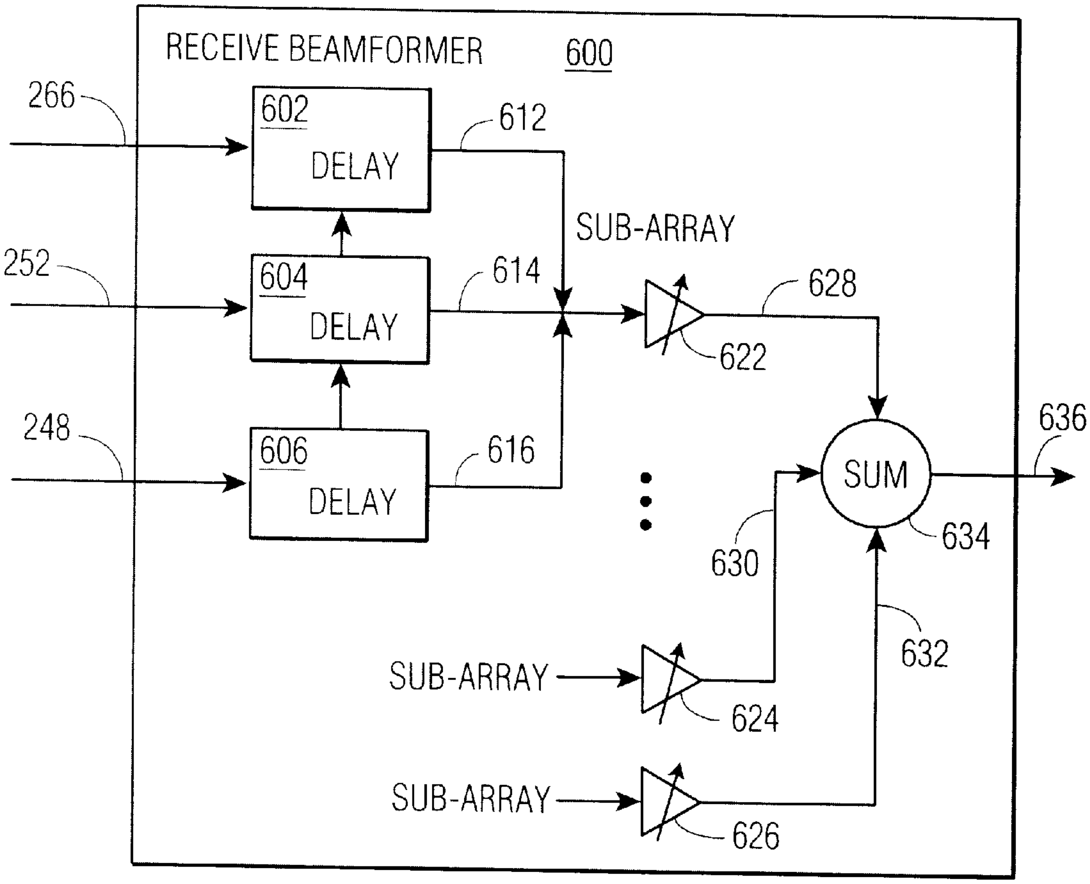
FIG. 6 is a schematic diagram illustrating an alternative embodiment of the receive beamformer of FIG. 2.

FIG. 6 is a schematic diagram illustrating an alternative embodiment of the receive beamformer of FIG. 2. The receive beamformer 600 of FIG. 6 includes a plurality of delay elements, three of which are illustrated using reference numerals 602, 604 and 606. Each of the delay elements receives an input via connections 266, 252 and 248, from a respective transducer element. The inputs 266, 252 and 248 are the same inputs received from the variable receive amplifiers 264, 242 and 246, respectively, of FIG. 2. However, in the receive beamformer 600, the outputs of each delay element 602, 604 and 606 on lines 612, 614 and 618, respectively, are formed into a subarray. The subarray signal is supplied to variable gain amplifier 622. Although omitted for simplicity from FIG. 6, similar subarray signals are supplied to variable gain amplifiers 624 and 626. Further, many additional subarray signals can be supplied to many additional variable gain amplifiers, the detail of which is omitted in FIG. 6.

The output of each of the variable gain amplifiers 622, 624 and 626 is supplied via connections 628, 630 and 632, respectively, to summing element 634. Summing element 634 adds all of the beamformed, subarray signals and supplies a single beamformed output on connection 636. Further, in other alternative embodiments of the receive beamformer 600, the variable gain amplifiers can be provided prior to the delay elements and the outputs of the variable gain amplifiers can be combined into subarray signals prior to application to the delay elements. In such an embodiment, additional delay elements after (or before) the variable gain amplifiers reduce the delay requirement of the delays 602, 604 and 606, so the delays can be economically implemented in analog circuitry. When a reasonable number of subarrays have been formed, there will be a lesser number of large delays applied to each subarray. Indeed, in such an embodiment, the subarray signals could be converted to digital form before the final delay and sum.

It will be apparent to those skilled in the art that many modifications and variations may be made to the preferred embodiments of the present invention, as set forth above, without departing substantially from the principles of the invention. For example, the invention can be used to provide variable and selectable two-dimensional apodization control in an ultrasonic transducer having micro-machined ultrasonic transducer elements or piezoelectric elements. All such modifications and variations are intended to be included herein within the scope of the present invention, as defined in the claims that follow.

What is claimed is:

1. An apparatus for providing multi-dimensional apodization control in an ultrasonic transducer, comprising:

an ultrasonic transducer array having a plurality of individually controllable ultrasonic transducer elements distributed in at least two dimensions; and control circuitry associated with each of the individually controllable ultrasonic transducer elements and configured to allow selective multi-dimensional apodization of all dimensions of an aperture of the multi-dimensional ultrasonic transducer array such that all of the ultrasonic transducer elements are controllable during each apodization.

2. The apparatus of claim 1, wherein the ultrasonic transducer array further comprises micromachined ultrasonic transducer (MUT) elements.

3. The apparatus of claim 2, wherein the MUT elements are arranged in a matrix array.

4. The apparatus of claim 1, wherein the ultrasonic transducer array further comprises piezoelectric elements.

5. The apparatus of claim 1, wherein the control circuitry associated with each of the individually controllable ultrasonic transducer elements allows partially sampled arbitrary multi-dimensional apodization of all dimensions of an aperture of the ultrasonic transducer array.

6. The apparatus of claim 1, wherein the control circuitry associated with each of the individually controllable ultrasonic transducer elements allows fully sampled arbitrary multi-dimensional apodization of all dimensions of an aperture of the ultrasonic transducer array.

7. The apparatus of claim 1, wherein the selective apodization of all dimensions of an aperture of the ultrasonic transducer array varies between a transmit cycle and a receive cycle.

8. The apparatus of claim 1, wherein the selective apodization of all dimensions of an aperture of the ultrasonic transducer array varies during a receive cycle.

9. The apparatus of claim 1, wherein the selective apodization of all dimensions of an aperture of the ultrasonic transducer array is a non-separable function of the multiple dimensions of the multi-dimensional ultrasonic transducer array.

10. The apparatus of claim 1, wherein the selective apodization of all dimensions of an aperture of the ultrasonic transducer array forms a sparsely sampled aperture having arbitrary size, shape and sampling.

11. The apparatus of claim 1, wherein at least one dimension of the ultrasonic transducer array is curved.

12. A method for controlling apodization in an ultrasonic transducer, comprising the steps of:

providing an ultrasonic transducer array having a plurality of individually controllable ultrasonic transducer elements distributed in at least two dimensions; and controlling each of the plurality of individually controllable ultrasonic transducer elements to allow selective multi-dimensional apodization of all dimensions of an aperture of the ultrasonic transducer array such that all of the ultrasonic transducer elements are controllable during each apodization.

13. The method of claim 12, wherein the ultrasonic transducer array further comprises micromachined ultrasonic transducer (MUT) elements.

14. The method of claim 13, further comprising the step of arranging the MUT elements in a matrix array.

15. The method of claim 12, wherein the ultrasonic transducer array further comprises piezoelectric elements.

16. The method of claim 12, further comprising the step of allowing partially sampled arbitrary multi-dimensional apodization of all dimensions of an aperture of the ultrasonic transducer array.

17. The method of claim 12, further comprising the step of allowing fully sampled arbitrary multiple dimensional apodization of all dimensions of an aperture of the ultrasonic transducer array.

18. The method of claim 12, further comprising the step of varying the selective apodization of all dimensions of an aperture of the ultrasonic transducer array between a transmit cycle and a receive cycle.

19. The method of claim 12, further comprising the step of varying the selective apodization of all dimensions of an aperture of the ultrasonic transducer array during a receive cycle.

20. The method of claim 12, wherein the selective apodization of all dimensions of an aperture of the ultrasonic transducer array is a non-separable function of the multiple dimensions of the ultrasonic transducer array.

21. The method of claim 12, further comprising the step of forming a sparsely sampled aperture having arbitrary size, shape and sampling.

22. The method of claim 12, wherein at least one dimension of the ultrasonic transducer array is curved.

* * * * *